United States Patent [19]

Gustafson et al.

[11] Patent Number: 5,203,340
[45] Date of Patent: Apr. 20, 1993

[54] APPARATUS FOR REZEROING AN IN VIVO PRESSURE SENSOR AND METHOD FOR REZEROING

[75] Inventors: Gary E. Gustafson, Sandy; Wallace H. Ring; Timothy J. Erskine, both of Salt Lake City; Kim L. Richardson, Herriman; Steven C. Kimble, Draper, all of Utah

[73] Assignee: Becton, Dickinson and Company, Franklin Lakes, N.J.

[21] Appl. No.: 851,712

[22] Filed: Mar. 16, 1992

Related U.S. Application Data

[63] Continuation of Ser. No. 578,712, Sep. 7, 1990, Pat. No. 5,133,358.

[51] Int. Cl.$^5$ .................... A61B 5/02; A61M 25/00
[52] U.S. Cl. ............................. 128/675; 73/4 R
[58] Field of Search ............... 128/673, 674, 675, 748; 73/4 R, 708

[56] References Cited

U.S. PATENT DOCUMENTS

| | | |
|---|---|---|
| 3,545,275 | 12/1970 | Harrison et al. |
| 3,811,427 | 5/1974 | Kresse |
| 3,831,588 | 8/1974 | Rindner ........................ 128/675 |
| 3,911,902 | 10/1975 | Delpy ........................... 128/675 |
| 4,274,423 | 6/1981 | Mizuno et al. ............... 128/675 |
| 4,342,218 | 8/1982 | Fox |
| 4,603,699 | 8/1986 | Himpens ..................... 128/673 X |
| 4,610,256 | 9/1986 | Wallace ...................... 128/673 X |
| 4,722,348 | 2/1988 | Ligtenberg et al. |
| 4,809,704 | 3/1989 | Sogawa et al. |
| 4,809,709 | 3/1989 | Brooks |
| 4,886,070 | 12/1989 | Demarest |

FOREIGN PATENT DOCUMENTS 1261775 1/1972 United Kingdom ................ 128/675

Primary Examiner—V. Millin
Assistant Examiner—Sebastiano Passaniti
Attorney, Agent, or Firm—Aaron Passman; Michael G. Schwarz

[57] ABSTRACT

A sensor assembly for an in vivo physiological pressure measurement has a member with a distal end to ease placement of the catheter sensor assembly in vivo. A passage is preferably in an intermediate part of the member and is open but covered by a pressure responsive sensor sealing the passage. The sensor has a first side away from the intermediate part for exposure to in vivo physiological pressure and a second side in fluid communication with the passage. A pressure connecting means for inhibiting liquid communication located between the physiological pressure and the passage is arranged for selectively connection therebetween so that when connected the pressure on the first and second sides of the sensor can be substantially equalized. A control ex vivo makes the selective connection of the second side of the pressure sensor and the physiological pressure. A method for rezeroing an in vivo pressure sensor has the steps of obtaining a signal from the first side of the sensor at distal end, using a pressure substantially equal to the in vivo pressure and applying that pressure to the second side of the sensor.

12 Claims, 3 Drawing Sheets

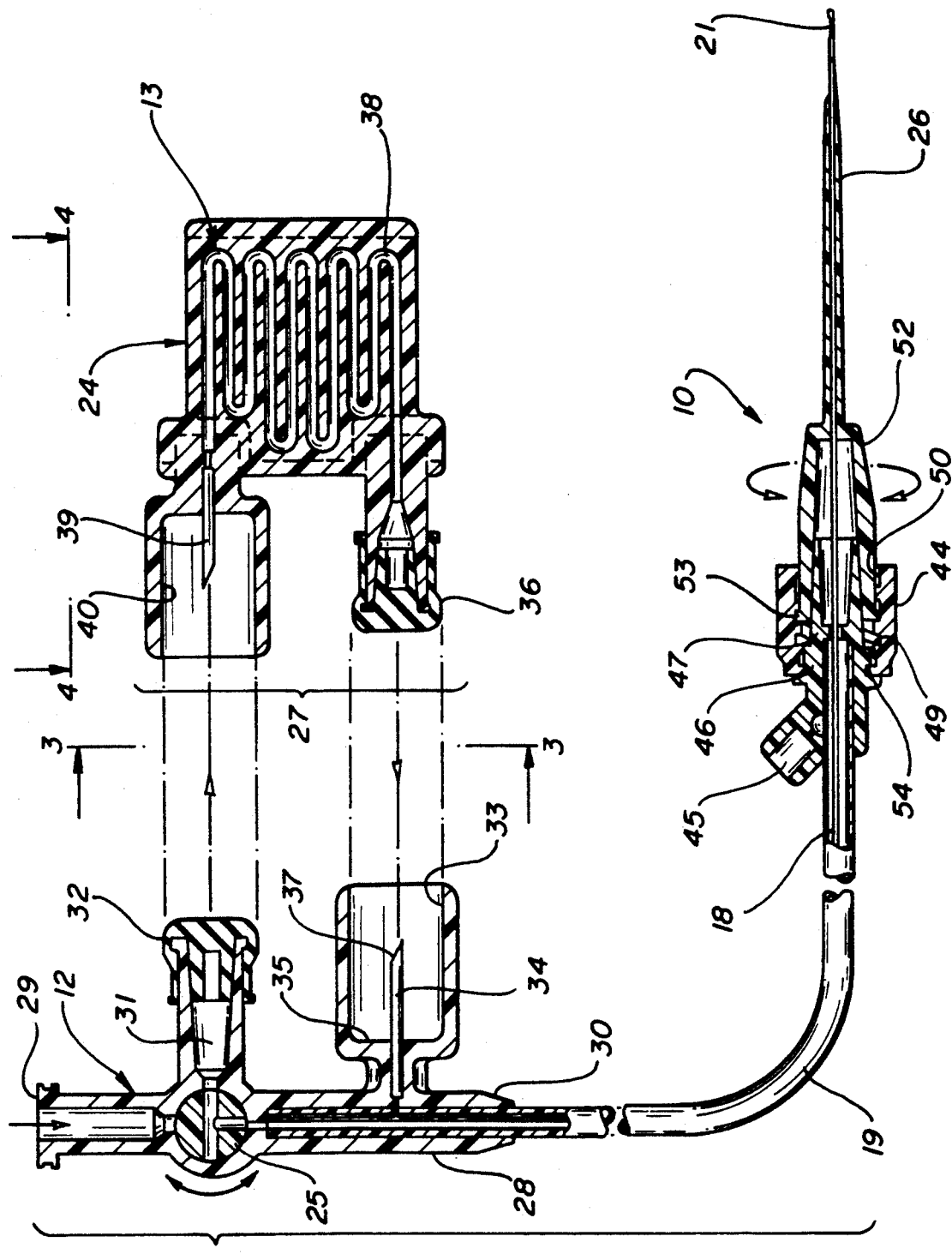

APPARATUS FOR REZEROING AN IN VIVO PRESSURE SENSOR AND METHOD FOR REZEROING

This is a continuation of application Ser. No. 07/578,712, filed Sep. 7, 1990 now U.S. Pat. No. 5,133,358.

BACKGROUND OF THE INVENTION

1. Field of the Invention.

This invention relates to a catheter or probe with a sensor for placement within a human or animal to allow direct monitoring within the body, and more particularly, relates to rezeroing of the pressure sensor in vivo and a method of rezeroing the sensor in vivo.

2. Background

Catheters have been inserted into humans and animals for diagnosis, monitoring and treatment purposes and such catheters have to be small and flexible in size and structure in order to function without irritating the body part into which they are placed. Typically, catheters are used to infuse medications or remove samples for purposes of analysis. Multilumen catheters are sometimes used to infuse medication and remove samples at the same time.

If a sample is removed for purposes of analysis, it has to be taken to a laboratory, analysis made and the results transmitted to the doctor. Delay in performing the analysis and transmitting the data sometimes can be fatal to the patient. Another use of a catheter is to form a hydraulic column for transmitting pressure readings to an external sensor. In connection with pressure sensors, the hydraulic column has problems of air bubbles, kinks in the tubing of the column and blood clots, each of which tend to affect the reliability, waveform fidelity, the accuracy and precision of the readings.

Current technology uses a 20 gauge catheter to introduce therapy or provide diagnosis. This size is easily inserted and easy to use without irritation or injury to the body. Twenty gauge catheters are commonly used on all but pediatric patients without problems of introduction or irritation in connection with peripheral vessels. A pressure sensor on the distal tip of a 20 gauge catheter or probe would eliminate the mentioned hydraulic column difficulties.

Catheter tip pressure sensors have heretofore been rezeroed by zeroing ex vivo, by placing a known pressure on each side of the sensor. Those rezeroing techniques have difficulties in connection with accuracy, infection control and ease of use. The sensor may include a semiconductor with a pressure responsive circuit located on the tip of a catheter.

Catheters having sensors are known and include sensors mounted at the distal tip of the catheter. U.S. Pat. No. 3,710,781 shows a catheter tip pressure sensor wherein a pair of elongate pressure sensor elements are mounted on opposite sides of a support. This is done to permit as large a sensor area as practical for purposes of providing accurate reproductions of blood pressure waveforms. U.S. Pat. No. 3,545,275 shows a device responsive to impedance used for measuring pressure with a miniaturized sensor. The sensor is responsive to diaphragm fluctuations where the diaphragm is mounted in the distal end of a small diameter tube. A small probe is disclosed in U.S. Pat. No. 3,811,427 wherein a pair of electrodes are mounted in a liquid filled chamber and are sensitive to fluctuations in a diaphragm mounted at the distal end of a catheter tube. The probe is said to be smaller than one millimeter. Two embodiments are shown. Each has a diaphragm in the distal end of the catheter and a longitudinal separator which carries the pressure responsive means and isolates the liquid from the remainder of the catheter such that fluctuations in the diaphragm are transmitted to the separator which is generally longitudinally disposed.

U.S. Pat. No. 4,722,348 shows a semiconductor mounted within a tubular housing in the end of the catheter tube and having a pressure inlet. Sealant protects the semiconductor which is held to the support by the double face adhesive tape which also carries the electrical conductors. U.S. Pat. No. 4,809,704 discloses catheters with the sensor mounted in the tip of the catheter supported on a base by a potting resin carried within the catheter tube. The resin is a urethane or silicone material about the sensor with appropriate openings for sampling. Assembly of the sensors within the catheters has been slow and labor intensive.

The offset pressure due to changes in atmospheric pressure has to be accounted for in that the reference side of the sensor is considered an essentially zero pressure. U.S. Pat. No. 4,672,974 has an apparatus with a port for a substitute reference pressure and an external pressure gauge for measuring the mean pressure through an auxiliary lumen of the catheter. Thus, a known pressure can be substituted for atmospheric pressure in the process of rezeroing the offset pressure. U.S. Pat. No. 4,712,566 has a sensor carried on a guide which is moveable in and out of the catheter tube so that the in vivo side of the sensor may be brought into the catheter removed from blood pressure and subjected to a generated pressure during calibration. The guide and catheter cooperate with one another to seal off the sensor during rezeroing.

U.S. Pat. No. 4,854,326 has an impedance variable transducer with a technique for zeroing the in vivo transducer by varying the static pressure in a reservoir connected to the transducer. Thus, changes in the height of the reservoir can be used to adjust the zero point of the transducer. This approach, although feasible, introduces another variable into the system. In addition, a gas retaining flexible membrane has to be located in the liquid filled lumen to the reservoir. The membrane is to separate the liquid from the gas filled lumen. The flexible membrane is said to prevent oscillating movement of the liquid in the lumen as a result of the interchange of energy by the liquid, the displacement of the diaphragm in the transducer and the compliance of the lumen about the liquid. Isolation is not the purpose of the flexible membrane.

SUMMARY OF THE INVENTION

The preferred catheter sensor assembly for in vivo rezeroing and physiological pressure measurement has a member with a distal end to ease placement of the catheter sensor assembly into an in vivo site. The sensor assembly having an intermediate part extending to a proximal end for fluid connection of the member with a lumen of a tube which extends from the proximal end. A passage is preferably in the intermediate part and is opened in a first direction. The passage extends through the proximal end and across the intermediate part. A pressure responsive sensor covers and seals the passage; the sensor having a first side facing the first direction away from the section for exposure to in vivo physiological pressure. The sensor has a second side opposite the first side; the second side is in fluid communication with the passage, the lumen and the tube.

A pressure connecting means for inhibiting liquid communication is preferably located between the in vivo physiological pressure obtained from a catheter and the tube to substantially isolate the second side of the sensor from liquid communication with the physiological pressure when the first and second sides of the sensor are subject to the in vivo pressure. The in vivo pressure on the sides of the sensor may be used for the determination of a datum value of a signal from the sensor. A control may be associated with the catheter and the pressure connecting means for inhibiting liquid communication has a portion positioned ex vivo so that the selective connection of the second side of the pressure sensor and the physiological pressure can be made ex vivo.

In the preferred embodiment, the portion may be located next to the pressure connecting means for inhibiting liquid communication and remote relative to the sensor. It is preferred to have a pressure sensing device sealed to the intermediate part and responsive to the pressure differential between the in vivo physiological pressure on the first side and the pressure in the passage. The preferred datum value is the zero offset of the semiconductor chip. The member is positioned in vivo and the portion ex vivo so that the selective operation of the control takes place ex vivo. A circuit connected to the semiconductor chip adjusts the value of signals of the pressure differential to account for the datum value so that precise readings of the in vivo physiological pressure may be made. The sensor may be capacitive, half bridge, optical or ultrasonic. The semiconductor chip most preferably has a Wheatstone bridge circuit to provide signals that vary with the pressure differential across the sensor.

The pressure connecting means for inhibiting liquid communication may include a circuitous path as a barrier to liquid flow but not to pressure between the first and second sides. The tube extends from a connector and the adapter may have a port in fluid communication with the lumen and may also extend from the connector. The in vivo pressure applicable to the passage and the second side of the sensor may be arranged for selective application by a control most preferably including a multiposition valve for connecting the catheter to the circuitous path or atmosphere. To rezero the tube is connected to the circuitous path so that pressure from the catheter through the control passes through the circuitous path before reaching the tube. The multiposition valve is used to apply the physiological pressure to both sides of the sensor diaphragm. The time average of the output signal of the sensor will be the zero datum value.

The control may have a portion ex vivo so that a selection may be made from a location remote relative to the sensor for determination of a datum value of the pressure signal while the sensor remains in vivo. The in vivo physiological pressure is most preferably and selectively provided through the circuitous path via the control. The circuitous path acts as a liquid barrier between the in vivo pressure and the second side of the sensor.

A method for rezeroing an in vivo pressure sensor is also a part of the preferred invention. The method comprises the steps of obtaining a signal from an in vivo sensor exposed on a first side to in vivo pressure. The next step of the method is selecting a pressure substantially equal to the in vivo pressure. The added step of applying this pressure to a second side of the sensor opposite the first side.

The method may also have the step of selecting the pressure by the step of connecting the second side to the in vivo pressure. This preferred method adds to the connecting step the added step of preventing liquid flow between the first and second sides of the sensor. The preferred method also may use the step of connecting by controlling the connection ex vivo. The step of controlling the connection is preferably performed by operating a valve. After determining a datum value of the zero offset and using the sensitivity of the sensor, then these values can be applied to signals measured to obtain a precise in vivo pressure.

BRIEF DESCRIPTION OF THE DRAWINGS

FIG. 2 is an enlarged plan view of the catheter tip pressure sensor and in vivo rezeroing assembly of FIG. 1 with parts in cross section including a catheter adapter, a multiposition valve and the circuitous path which is shown separated from the multiposition valve for illustrative purposes.

DETAILED DESCRIPTION

Figure 1:
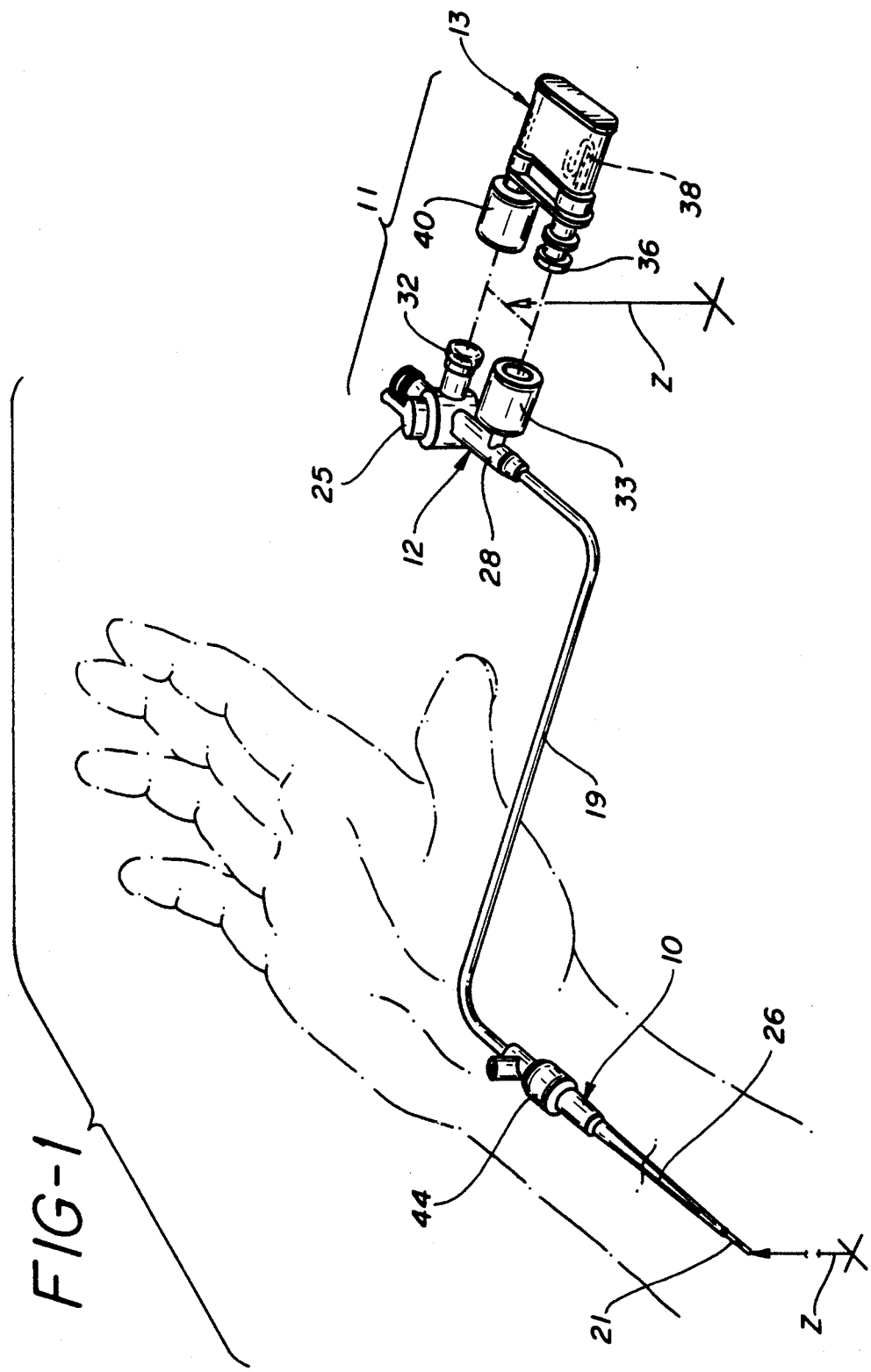
FIG. 1 is a perspective view of the catheter tip pressure sensor about to be connected to the preferred embodiment of an in vivo rezeroing assembly, the sensor is shown inserted into a patient and a circuitous path of the in vivo rezeroing assembly is shown maintained at the level of the in vivo sensor.

While this invention is satisfied by embodiments in many different forms, there is shown in the drawings and will herein be described in detail, a preferred embodiment of the apparatus and of the method, with the understanding that the present disclosure is to be considered as exemplary of the principles of the invention and is not intended to limit the invention to the embodiment illustrated. The scope of the invention will be measured by the appended claims and their equivalents.

Shown in FIG. 1 is a perspective view of the catheter tip pressure sensor 10 and the preferred embodiment of an in vivo rezeroing assembly 11. The catheter tip pressure sensor 10 is shown inserted into a patient's arm but may be inserted into any appropriate part of the vasculature of a human or animal. The inserted catheter tip pressure sensor 10 as when in vivo is maintained at the level "Z" of the in vivo rezeroing assembly 11 such that no additional pressure component is added because of any difference in elevation between the sensor 10 and the assembly 11.

FIG. 2 has an enlarged plan view of the catheter tip pressure sensor 10 and the in vivo rezeroing assembly 11 showing the relationship between a control or multipositioned valve 12 and a circuitous path 13. The valve 12 and the circuitous path 13 are parts of the in vivo rezeroing assembly 11. The valve 12 is arranged in fluid communication with the catheter tip pressure sensor 10 so that the in vivo physiological pressure can communicate with both sides of the sensor 10 or can be restricted to one side thereof whereby the zero offset may be determined and accounted for in connection with signals obtained from the sensor 10.

Figure 2A:
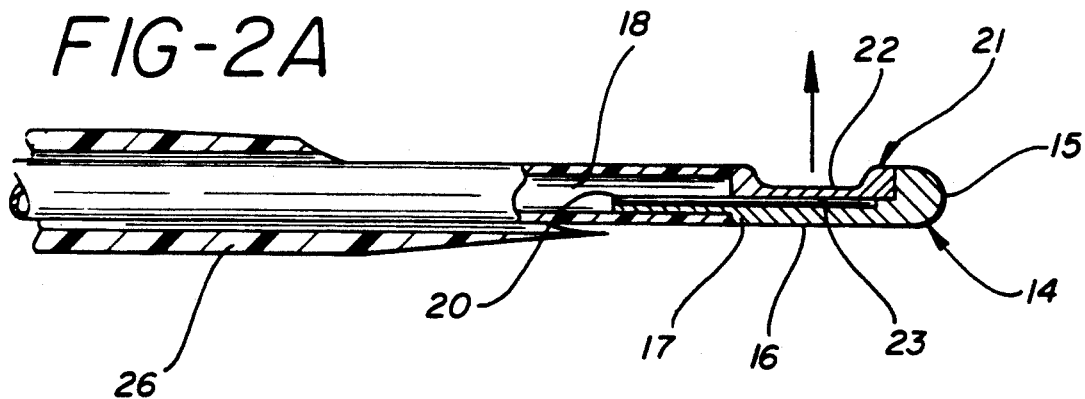
FIG. 2A is an enlarged view partially in cross section of the catheter tip pressure sensor.

In order to fully understand the in vivo rezeroing, an appreciation of the physical construction of a preferred embodiment of the catheter tip pressure sensor 10 is required. The catheter tip pressure sensor 10 is shown and described in detail in a pending application entitled, "Apparatus for a Catheter Sensor Support and Method for Using the Support," Ser. No. 410,564, filed on Sep. 21, 1989. The catheter tip pressure sensor described in that application is incorporated herein and made a part of this specification. As best seen in FIG. 2A, the catheter tip pressure sensor includes a member 14 with a distal end 15 to ease placement of the catheter tip sensor 10 into an in vivo site in the vasculature of a human or animal. An intermediate part 16 and a proximal end 17 on the member 14 are used to provide fluid connection with a lumen 18 of a tube 19 which extends from the proximal end 17. A passage 20 is provided through the intermediate part and opens in a first direction. The passage 20 extends through the proximal end 18 and across the intermediate part 16.

A pressure responsive sensor 21 such as a Wheatstone bridge is carried upon for covering and sealing the passage 20. While a Wheatstone bridge is preferred, it is recognized that miniaturized pressure sensing elements currently unavailable may in the future be used with the in vivo rezeroing assembly 11 herein described. The pressure responsive sensor 21 has a first side 22 facing a first direction "A", that is, away from the intermediate part 16 so as to be exposed to in vivo physiological pressure when positioned in the vasculature of a human or animal as shown in FIG. 1. The pressure responsive sensor 21 has a second side 23 opposite the first side 22. The second side 23 is in fluid communication with the passage 20 and the lumen 18.

A pressure connecting means 24 for inhibiting liquid communication is part of the in vivo rezeroing assembly and may be selectively connected to the lumen 18 to bring the first and second sides 22 and 23 of the pressure responsive sensor 21 into pressure communication with the in vivo physiological pressure. That is to say that the first side 22 of the pressure responsive sensor 21 is exposed to the in vivo conditions directly and the second side 23 may, by means of the valve 12, be connected to the in vivo physiological pressure by moving valve 12. The aforesaid connection is indirect in the sense that liquid is not permitted to reach the second side 23 of the sensor 21.

While a specific preferred embodiment of the pressure connecting means 24 for inhibiting liquid communication is shown and described, the in vivo rezeroing assembly as herein set forth includes any isolation arrangement which will allow indirect pressure communication but inhibit liquid migration to the second side 23 of the pressure responsive sensor 21. The pressure connecting means 24 for inhibiting liquid communication is in the preferred embodiment, circuitous path 13, however, an elongate tube, capillary or other means (not shown) which would act as a barrier to liquid communication such as a diaphragm or gas permeable liquid impermeable filter also not shown) may be used as the circuitous path 13. During in vivo rezeroing, the pressures on the first and second sides 22 and 23 of the sensor 21 can be substantially equalized by application of in vivo physiological pressure to both the first and second sides 22 and 23 while limiting the liquid communication to the second side 23. The objective is the determination of a datum value, indicative of the equalized pressure of the in vivo sensor 21, for zeroing the signals from the pressure responsive sensor 21 by moving valve 12.

Selective operation from an ex vivo site is required to make the in vivo rezeroing assembly safe to use at any time the pressure responsive sensor 21 is determined to be in need of rezeroing eve though the sensor 21 is still in the vasculature of a human or animal. Minimizing the handling of the catheter tip pressure sensor 10 prevents infection from migrating through the entry site of the catheter tip pressure sensor into the body. The valve 12 shown in FIGS. 1 and 2 is positioned ex vivo in association with the catheter tip pressure sensor 10. The valve 12 has a portion 25 to operatively connect with the pressure connecting means 24 for inhibiting liquid communication whereby selective communication of the second side 23 of the pressure sensor and the physiological pressure can be arranged as needed. The preferred selective control is with the multipositioned valve 12 which is a common accessory familiar to practitioners for use with other medical applications, such as thermodilution, external pressure monitoring or the like. The multiposition valve 12 is for convenience and clarity shown in FIG. 2 wherein the valve is in a first position such that in vivo pressure communication is permitted. Liquid flow through the circuitous path 13 is inhibited. The valve 12 may be rotated to in its second position wherein flow is not permitted to communicate with the circuitous path 13. The positioning of valve 12 when in its second position closes communication to circuitous path 13.

Also shown in FIG. 2 is a quick disconnect arrangement 27 at the interface of the circuitous path 13 and the multiposition valve 12. Specifically, a housing 28 of the multiposition valve includes a connector port 29, an inlet 30 from the lumen 18 and an outlet 31 covered by a pierceable septum 32. Carried on the housing 28 is a well 33 with a hollow needle 34 extending from the bottom 35 thereof and aligned for piercing a septum 36 on the circuitous path 13 as will be explained. The pierceable septum 32, the well 33 and needle 34 are positioned parallel to one another so that alignment and unidirectional movement is all that is required to conjugate the circuitous path 13 and the housing 28. An understanding of the quick disconnect arrangement 27 between the circuitous path 13 and the housing 28 will follow with the explanation of the conjugating parts of the circuitous path 13. The needle 34 passes through the bottom 35 of the well 33 and is in fluid communication with the lumen 18 so that pressure in the catheter lumen 18 is available to a bore 37 through the needle 34.

Figure 3:
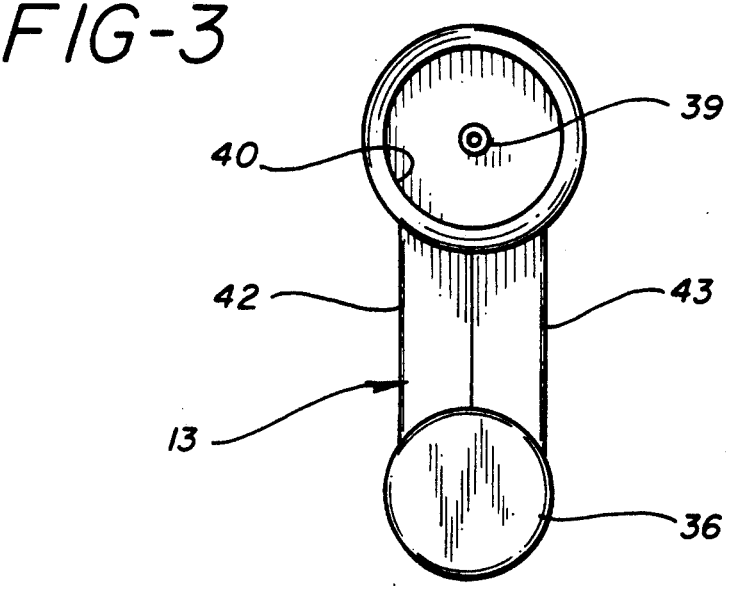
FIG. 3 is an end view in cross section of the circuitous path taken along line 4—4 of FIG. 2.
Figure 4:
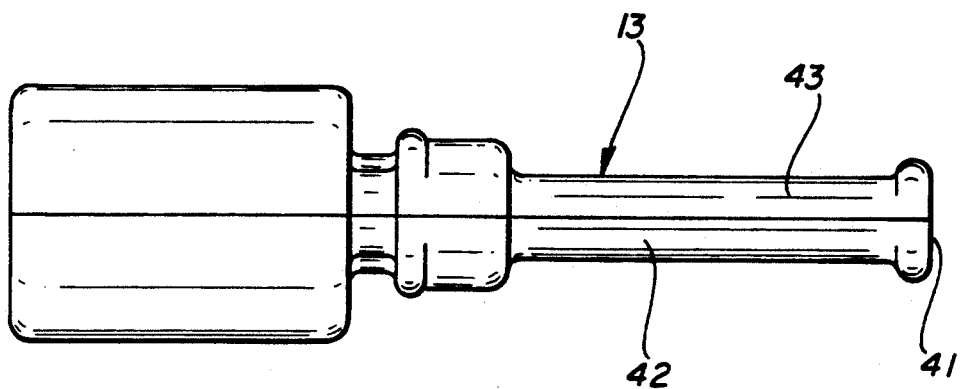
FIG. 4 is a side view in cross section of the circuitous path taken along line 3—3 of FIG. 2.

The circuitous path 13 is simply a labyrinth 38 between the pierceable septum 32 of the circuitous path 13 and a needle 39 in the well 40. That is to say that the circuitous path 13 has the fittings identical to those of the housing 28 such that the needle (either 34 or 39) on one may pierce the septum 32 or 36 on the other when the circuitous path 13 is aligned and the moved unidirectionally to conjugate with the housing 28. It is preferred that needle 34 pierce septum 32 before needle 39 pierce septum 36 to prevent circuitous path 13 from filling with fluid. After mating engagement, the catheter 26 is in fluid communication with the housing 28 and the labyrinth 38 of the valve is in the first position as shown in FIG. 2. Because of the tortuous configuration of the labyrinth 38 the physiological pressure in the catheter 26 is available to the well 40 and needle 39 of the circuitous path 13. Consequently, the circuitous path 13 acts as a barrier to the transmittal of liquid to the lumen 18. The preferred embodiment of the circuitous path 13 is shown in FIGS. 2, 3 and 4 as a combination 41 of an upper component 42 and a lower component 43 which are shaped to fit to each other and capture the hollow needle 39 at one end of the circuitous path 13 and retain the pierceable septum 36 at the other end of the circuitous path 13. The preferred components 42 and 43 are injection molded and designed and shaped to fit and be secured to one another by cement, glue, RF welding, solvent bonding or any other method that holds the components 42 and 43 together to make a leak free labyrinth 38 therethrough.

Alternatively, the circuitous path 13 may be made in accordance with the design shown and described in U.S. Pat. No. 4,919,134, Issued on Apr. 24, 1990, and entitled, "Thermoelectric Chiller and Automatic Syringe" which is incorporated herein and made a part of this specification. Although this construction is not the preferred embodiment, it is believed that the labyrinth 38 of that thermal formed plastic structure would work successfully. While a valve 12 is shown and described, the circuitous path 13 may be used without any valve to connect the first and second sides 22 and 23 of the sensor to physiological pressure. If there were no multi position valve 12 then the needle 34 on the housing 28 would exit to atmospheric pressure and the second side 23 would be subject to atmospheric pressure. Placement of the circuitous path 13 on the housing 28 would connect the physiological pressure to the second side 23. If pressure artifacts from up stream in a saline column are affecting the zero measurement, then valve 12 can be used to eliminate these artifacts connecting and allowing only physiological pressure to reach the first and second sides by changing valve 13 from its first position to its second position.

FIG. 3 is an enlarged view seen from lines 3—3 of FIG. 2 of the needle 39 and well 40 and the pierceable septum 36 as would be seen by one positioned at the housing 28 just prior to engagement of the circuitous path 13 with and the housing 28. Apparent from this view is the parallel positioning of the respective wells, needles and the septums. While the well and needle are concentric that is not essential just preferred as that arrangement centers the needles with respect to the septums. The preferred parallel arrangement allows the attachment of the circuitous path and housing by the simple application of unidirectional movement and pressure therebetween once alignment is made. The well 33 on the housing 28 and the well 40 on the circuitous path 13 each guide the opposing septums 36 and 32 onto the needles 34 and 39 during conjugation. The needles 34 and 39 are recessed slightly into their respective wells 33 and 40 whereby when each septum 32 and 36 first engages with its well 33 and 40, the contact therebetween centers the septum 36 and 32 so each is pierced through its middle by either needle 34 or 39. The recessing of the needles 34 and 39 protects the user and prevents accidental sticking. While circular cross sections for the wells and septums are shown, any shapes which are convenient to make and which fit during conjugation would be acceptable. Circular septums are common and therefore preferred.

FIG. 4 is an enlarged side view of the circuitous path 13 as seen from line 4—4 of FIG. 2. Apparent from FIG. 4 is the manner in which the upper component 42 and the lower component 43 fit together to provide a leak free labyrinth 38. The well 40 on the circuitous path 13 and its relationship to the labyrinth 38 are shown in the side view of FIG. 4. FIG. 3 has the end view of the circuitous path 13 and illustrates the parallel arrangement of the needle 39, well 40 and the septum 36.

The pending patent application entitled, "Apparatus and Method for Connecting a Passageway and Openings with a Connector", Ser. No. 246,476, filed on Sep. 19, 1988, discloses a connector such as 44 shown in FIG. 2. The disclosure and drawings of that patent application are incorporated herein by reference and made a part hereof. A proximal side port 45 is on connector 44. Connector 44 has a pair 46 of generally parallel passages through a central body connecting the proximal side port 45 with the catheter 26 to one passage through the central body 47 and the lumen 18 to the other passage through the central body 47.

Surrounding the central body 47 is a female luer nut 49 with an internal thread 50 arranged to rotate about the central body 47. Specifically, a male luer taper 51 on the distal inlet of the central body 47 is secured to a catheter adapter 52 having a female luer taper by the rotation of the luer nut 49. In use an entry passageway into the vasculature of the human or animal is provided by catheter 26 and adapter 52. Locking lugs 53 thread to the luer nut 49. The luer nut 49 is supported by a circular groove 54 on the central body 47 so that the luer nut 49 may turn freely without axial motion relative to the central body 47.

Skilled practitioners in the medical field will appreciate the manner of use of the catheter tip pressure sensor 10 during in vivo rezeroing and in particular, the safety and convenience of not having to remove the sensor 21 to rezero. Thus, the in vivo rezeroing assembly 11 shown and described herein provides freedom from infection due to handling and convenience of use. It is merely a simple matter of rotating the multi position valve 12 from position one to position two in order to connect the physiological pressure to both sides of the sensor and disconnect the vent to the second side 23 of the sensor 21.

A method for rezeroing the in vivo pressure sensor 11 is a part of the preferred embodiment and the method has the steps of obtaining a signal from the first side 22 the catheter tip pressure sensor 10 exposed to an in vivo physiological pressure. The next step of the preferred method requires transmitting a pressure substantially equal to the physiological pressure through the catheter 26 to and through the circuitous path 13. The step of applying the pressure in the circuitous path 13 to the lumen 18 to equalize the pressure on the second side 23 of the sensor 21 follows. The last step determines the signal with balanced pressure applied to the first and second sides 22 and 23 of the in vivo sensor 21 for use in correcting for zero offset.

The method may have the step of selecting the pressure including the step of removably and selectively connecting the catheter 26 to the circuitous path or to atmospheric pressure. The method could have the step of connecting wherein an additional step of inhibiting fluid communication between the catheter 26 and the lumen 18 is used. The method can include the added step of selectively connecting by controlling the connection ex vivo.

What is claimed is:

1. A device for re-zeroing a pressure sensing apparatus for measuring physiological pressure, said device comprising:
   a first pressure communication means for exposure to and communication of an in-vivo pressure;
   a second pressure communication means for exposure to and communication of a reference pressure;
   a pressure responsive sensor for measuring in-vivo physiological pressure, said sensor comprising a first side for exposure to the in-vivo pressure and a second side in pressure communication with the second pressure communication means;
   pressure resetting means for selectively applying the in-vivo pressure to the second side by selectively linking the first pressure communication means to the second pressure communication means, thereby making the reference pressure substantially equal to the in-vivo pressure,
   wherein the pressure resetting means comprises pressure interface means for communicating the in-vivo pressure between the first pressure communication means and the second side via the second pressure communication means such that the in-vivo pressure is applied to the second side and such that fluid does not flow across the pressure interface means.

2. The device of claim 1 wherein the pressure interface means comprises a circuituous path connectable between the first and second pressure communication means.

3. The device of claim 1 wherein the pressure interface means comprises a capillary tube connectable between the first and second pressure communication means.

4. The device of claim 1 wherein the pressure interface means comprises a diaphragm comprising first and second sides, the first side for pressure communication with the first pressure communicating means and the second side for pressure communication with the second pressure communication means.

5. The device of claim 1 wherein the pressure responsive sensor is located in-vivo and the pressure resetting means is actuated ex-vivo.

6. The device of claim 1 wherein the reference pressure is atmospheric pressure.

7. The device of claim 1 wherein the pressure interface means comprises a first port for connection to the first pressure communication means and a second port for connection to the second pressure communication means, the ports being configured such that the second port is connected to the second pressure communication means before the first port is connected to the first pressure communication means when the interface means is connected between the first and second pressure communication means.

8. The device of claim 1 wherein the pressure responsive sensor and the pressure interface means are at substantially the same elevation.

9. A method of re-zeroing a pressure sensing device for measuring physiological pressure, the method comprising:
   providing an in-vivo pressure responsive sensor, the sensor comprising a first side for exposure to an in-vivo pressure and a second side for exposure to a reference pressure;
   providing a first fluid communication means for exposure to an in-vivo pressure;
   communicating the reference pressure to the second side by a second fluid communicating means;
   interposing a pressure interface means between the first fluid communicating means and the second fluid communicating means so that the in vivo pressure is communicated to the second side in substitution for the reference pressure and so that liquid does not pass between the first and second pressure communicating means.

10. The method claim 9 further comprising the steps of using the in vivo pressure as a datum to correct for zero offset error.

11. The method of claim 9 wherein the step of interposing the pressure interface means is performed ex-vivo.

12. The method of claim 11 wherein the step of interposing is performed at an elevation equal to that of the in-vivo pressure responsive sensor.

* * * * *